(12) United States Patent
Evdokimov et al.

(10) Patent No.: US 9,095,429 B2
(45) Date of Patent: Aug. 4, 2015

(54) HEART VALVE PROSTHESIS

(75) Inventors: Sergey Vasilyevich Evdokimov, Penzenskaya Oblast (RU); Alexandr Sergeyevich Evdokimov, Penzenskaya Oblast (RU); Eduard Yurievich Goncharov, Penza (RU); Alexandr Nikolayevich Filippov, Penza (RU)

(73) Assignee: MedEng, Penza (RU)

( * ) Notice: Subject to any disclaimer, the term of this patent is extended or adjusted under 35 U.S.C. 154(b) by 1416 days.

(21) Appl. No.: 12/506,563

(22) Filed: Jul. 21, 2009

(65) Prior Publication Data

US 2010/0023121 A1    Jan. 28, 2010

(30) Foreign Application Priority Data

Jul. 23, 2008 (RU) ............................... 2008130562

(51) Int. Cl.
*A61F 2/24* (2006.01)
(52) U.S. Cl.
CPC ....... *A61F 2/2403* (2013.01); *A61F 2220/0091* (2013.01)
(58) Field of Classification Search
CPC .............. A61F 2/2403; A61F 2002/30471; A61F 2002/30624; A61F 2220/0091
USPC ............ 623/2.2, 2.22, 2.23, 2.27, 2.34
See application file for complete search history.

(56) References Cited

U.S. PATENT DOCUMENTS

| 4,878,909 | A | 11/1989 | Parravacini |
| 4,908,028 | A | 3/1990 | Colon et al. |
| 5,123,918 | A | 6/1992 | Perrier et al. |
| 6,896,700 | B2 * | 5/2005 | Lu et al. ............. 623/2.34 |
| 2009/0118824 | A1 | 5/2009 | Samkov |

FOREIGN PATENT DOCUMENTS

| EP | 0283413 | 9/1988 |
| RU | 2113191 | 6/1998 |
| WO | 01/43666 | 6/2001 |

OTHER PUBLICATIONS

European Search Report for EP 09009095.2, dated Sep. 14, 2009.

* cited by examiner

*Primary Examiner* — Brian Pellegrino
(74) *Attorney, Agent, or Firm* — Bachman & LaPointe, P.C.

(57) ABSTRACT

A medical device in cardiac surgery for replacement of the diseased native heart valves in humans increases thromboresistance of heart valve prosthesis. A heart valve prosthesis comprising an annular housing with the inner surface defining the blood flow I through the valve prosthesis and leaflets mounted within the annular housing with the possibility to pivot around the reference axis between an open position which allows the passage of the direct blood flow I, and a closed position which restricts the blood backflow II. Each leaflet has an upstream surface facing the direct blood surface I, a downstream surface facing the blood backflow II, a coaptation surface, and a side surface.

4 Claims, 2 Drawing Sheets

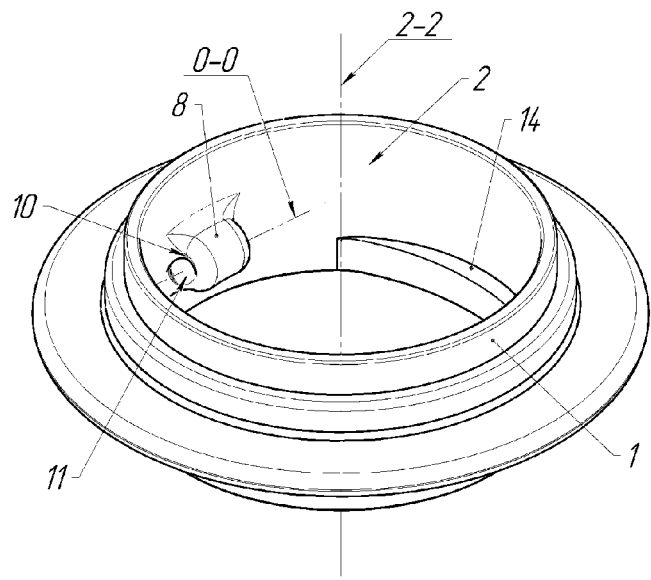
Fig. 3
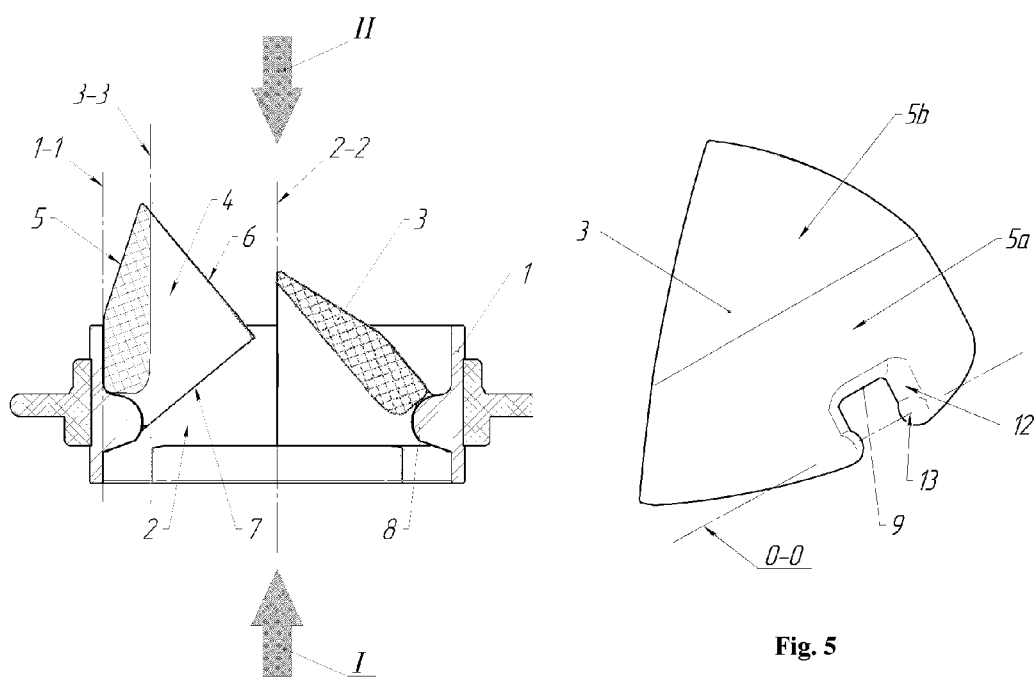
Fig. 4
Fig. 5

HEART VALVE PROSTHESIS

BACKGROUND OF THE INVENTION

The invention relates to medical devices and can be used in cardiac surgery for replacement of the diseased native aortic and mitral heart valves in humans. This invention can also be successfully used for replacement of the diseased tricuspid valve.

There is a certain heart valve prosthesis [1] comprising an annular housing with fixing elements restricted by support surfaces facing the direct and reverse blood flow and a side surface facing the central axis of the housing, and leaflets mounted within the annular housing with the possibility to pivot between an open position, which allows the passage of the direct blood flow, and a closed position which restricts the blood backflow, each leaflet has an outer side surface having projections with support surfaces facing the direct blood flow, which interact with the corresponding support surfaces of said fixing element of the housing, a coaptation surface interacting with the corresponding coaptation surface of the other leaflet in the closed position, with projections having support surfaces facing the blood backflow and interacting with the support surface of the fixing element of the housing, an upstream and a downstream surfaces respectively facing the direct blood flow and the blood backflow, while the downstream surfaces of the leaflets have projections-cams which prevent the coaptation of the leaflets in the open position and restrict the opening angle of the leaflets.

This prosthesis, as experience of its clinical application had shown, has good hemodynamic characteristics and a small percentage of thrombotic and thromboembolic complications. However, its leaflets, which divide the hydraulic orifice of the housing into three segments, disrupt the homogeneous laminar structure of blood flow with creation of blood stagnation zones and thus preserving the possibility of thrombotic complications.

There is a certain heart valve prosthesis [2] comprising an annular housing, leaflets with the possibility to pivot and form a major zone of central passageway of the housing, and leaflet pivoting limiters. The leaflet pivoting limiters are represented by two pairs of projections located at the end surface of the housing facing the downstream blood flow, and which ensure limiting of their pivoting angle and permanent link with the housing by interacting with the side surfaces of the leaflets.

This prosthesis provides withdrawal of the leaflets from the housing orifice and therefore increases the homogeneousness of the flow structure. However the provision of the leaflet pivoting limiters at the end surface of the housing increases the prosthesis overall dimensions and risk of restriction of leaflet mobility by the internal heart structures.

This heart valve prosthesis was chosen by us as prototype prosthesis.

The objective of the proposed invention is to increase thromboresistance of prosthetic heart valve.

SUMMARY OF THE INVENTION

Proposed is a heart valve prosthesis comprising an annular housing with an inner surface defining the blood flow through the prosthesis, and leaflets mounted within the annular housing with the possibility to pivot around the reference axis of rotation between an open position, which allows the passage of the direct blood flow, and a closed position which restricts the blood backflow, each leaflet has an upstream surface facing the direct blood flow, a downstream surface facing the blood backflow, a coaptation surface interacting with the corresponding coaptation surface of the other leaflet in the closed position, and a side surface interacting with the inner surface of the housing. At least two console projections radially oriented and directed mainly perpendicular to the reference axis of leaflet rotation are provided at the inner surface of the housing, and a slot embracing the corresponding console projection of the housing is provided at each leaflet. The surfaces interacting with the leaflet slots and forming a supporting part of the hinge are provided at the lateral sides of the console projections and the counterpart surfaces forming a mobile part of the hinge and facing the side surfaces of the corresponding console projection are provided at the slot inner sides of each leaflet.

Furthermore the inner surface of the housing is mainly cylindrical and the downstream surface of each leaflet is formed by the crossing cylindrical and conical surfaces. In this connection the diameter of the cylindrical downstream surface of the leaflet corresponds to the diameter of the inner surface of the housing, and in the closed position of the leaflet the generatrix of the cylindrical downstream surface is approximately parallel to the central axis of the housing.

The upstream surface of each leaflet is provided in the form of cylindrical surface with diameter equal to or somewhat bigger than the diameter of the inner surface of the housing, and in the open position of the leaflet the generatrix of the cylindrical upstream surface is approximately parallel to the central axis of the housing.

The optimal embodiment of the hinges between the leaflets and the housing is an embodiment where the surfaces forming the supporting part of the hinge of the console projections are made as a segment of the spherical recess and the counterpart surfaces forming the mobile part of the hinge are made as a segment of the spherical projection.

However the above-mentioned embodiment of the hinges does not restrict the subject matter of the invention and the interacting hinge surfaces may be of any other form, for example as segments of cylindrical surfaces.

Ledges interacting with the side surfaces of the leaflets in the closed position are also provided on the inner surface of the housing.

Without restricting the subject matter of the invention, two, three or more leaflets may be mounted within the heart valve prosthesis. It would be reasonable to mount two leaflets for mitral and tricuspid prostheses and three leaflets for aortic prosthesis.

In the proposed heart valve prosthesis there are no elements which introduce disturbances into the blood flow or generate stagnation zones, thus ensuring higher thromboresistance of the prosthesis.

The provision of the console projections radially oriented and directed mainly perpendicular to the reference axis of rotation of the leaflets at the inner surface of the housing and the counterpart slot embracing the corresponding console projection of the housing at each leaflet ensures the mobile connection of leaflets with the housing. Moreover, if compared to the prototypes, the number of the hinged joints for one leaflet is twice as less. Due to this the thromboresistance of the prosthesis is increased because said hinged joints are the major potentially dangerous locations for thrombus formation and traumatization of blood elements.

The provision of the surfaces, which interact with the leaflet slots at the lateral sides of the console projections of the housing and form the supporting part of the hinge, and the counterpart surfaces, which face the side surfaces of the corresponding console projection of the housing and form the mobile part of the hinge at the inner slot sides, allows the leaflet to pivot around the hinge axis between the open and closed positions. Thus fulfilling the major intended function of the valve, i.e. to pass the direct blood flow and restrict the blood backflow.

The provision of the mainly cylindrical inner surface of the housing together with the downstream surface of each leaflet in the form of crossing cylindrical and conical surfaces with the diameter equal to the diameter of the inner surface of the housing ensures mutual conformity of said surfaces. Namely: because the central axis of the cylindrical downstream surface of the leaflet in the open position is parallel to the central axes of the housing, its cylindrical downstream surface fits closely to the inner surface of the housing practically along its whole perimeter, thus preventing the possibility of generation of any obstacles to the blood flow. Because the other part of the cylindrical downstream surface is conical it provides a surface inclined to the flow axis, which facilitates quick leaflet pivoting and valve closure under the influence of the blood backflow. The proposed embodiment of the downstream leaflet surface is an optimal one, but, without restricting the subject matter of the invention, it may be formed with other surfaces, for example, spherical, toroidal, conical ones, or in the form of two crossing cylindrical surfaces.

The provision of the upstream surface of each leaflet in the form of the cylindrical surface with the diameter equal or somewhat bigger than that of the inner surface of the housing ensures creation of the approximately cylindrical hydraulic orifice which allows the direct blood flow to pass freely through it when the leaflets are in the open position. The provision of the central axis of the upstream cylindrical surface of the leaflet in the open position approximately parallel to the central axis of the housing prevents creation of the extra orifice confuserness which can lead to additional energy losses.

The provision of the ledges at the inner surface of the housing, which interact with the side surfaces of the leaflets in the closed position, prevents leaflet escape from the housing.

Said features of the prosthesis ensure the creation of positive effect, that is a higher thromboresistance, better structure of the blood flow, and less trauma to formed elements of the blood.

BRIEF DESCRIPTION OF THE DRAWINGS

The invention is described by means of the following drawings, wherein

FIG. 3 is a perspective view of the annular housing of the heart valve of FIG. 2.

FIG. 4 is a cross-sectional view of the heart valve prosthesis taken along its centre plane.

FIG. 5 is a perspective view of the leaflet of the heart valve of FIG. 2.

DETAILED DESCRIPTION

Figure 1:
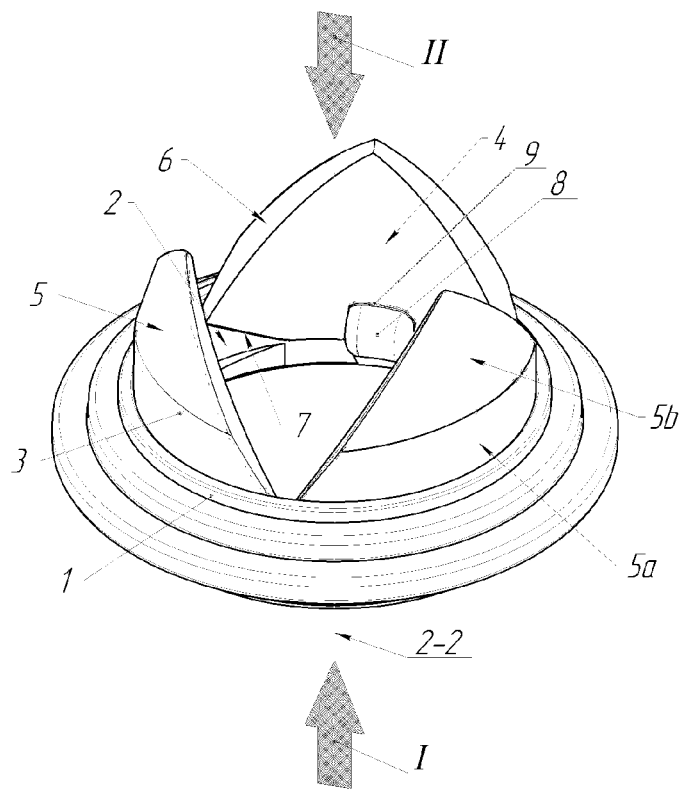
FIG. 1 is a perspective view the prosthesis with three leaflets shown in the open position.
Figure 2:
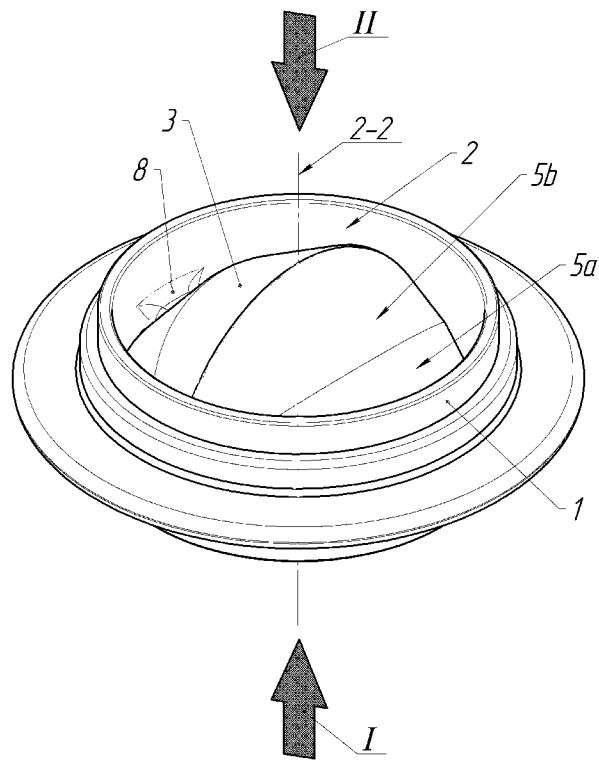
FIG. 2 is a perspective view of the prosthesis with two leaflets shown in the closed position.

For convenience in the drawings the direct blood flow is shown by the arrow I and the blood backflow by the arrow II.

The heart valve prosthesis comprising of the annular housing 1 with the inner surface 2, defining the blood flow I through the valve prosthesis, and the leaflets 3 mounted within the annular housing 1 with the possibility to pivot around the reference axis of rotation (shown by the dash-and-dot line 0-0) between the open position, which allows the passage of the direct blood flow I, and the closed position which restrict the blood backflow II. Each leaflet 3 has the upstream surface 4 facing the direct blood flow I, the downstream surface 5 facing the blood backflow II, the coaptation surface 6, and the side surface 7.

The console projections 8 radially oriented are provided at the inner surface 2 of the housing 1, and the slot 9, which corresponds to the projection, is provided at each leaflet.

The concave spherical surfaces 11 forming the supporting part of the hinge are provided at the lateral sides 10 of the console projections 8, while the counterpart convex spherical surfaces 13 are provided at the inner sides 12 of the slot 9 of each leaflet 3.

The inner surface 2 of the housing 1 is mainly cylindrical, and the downstream surface 5 of each leaflet 3 is in the form of the crossing cylindrical 5a and conical 5b surfaces, in this connection the generatrix (shown by the dash-and-dot line 1-1) of the cylindrical 5a downstream surface 5, is parallel to the central axis (shown by the dash-and-dot line 2-2) of the housing 1 (see FIG. 4).

The upstream surface 4 of each leaflet 3 is cylindrical, and when the leaflet 3 is in the open position its generatrix (shown by the dash-and-dot line 3-3) is approximately parallel to the central axis 2-2 of the housing 1.

The ledges 14 are provided at the inner surface 2 of the housing 1.

The heart valve prosthesis functions as follows.

When excess pressure is created at the inlet of the prosthesis the leaflets 3 pivot around the axis of rotation 0-0, and the convex spherical surfaces 13 in the leaflet slots 9 interact with the concave spherical surfaces 11 of the console projections 8 at the inner surface 2 of the housing 1 forming a hinge which provides a mobile connection of the leaflets 3 with the housing 1. When the cylindrical surfaces 5a of the leaflets 3 contact the inner surface 2 of the housing the pivoting of the leaflets 3 around the axis 0-0 stops. The heart valve prosthesis opens and allows the passage of the direct blood flow I. In this connection the direct blood flow I is restricted by the cylindrical upstream surfaces 4 of the leaflets 3, which define the central axisymmetric laminar blood flow I without introduction of any disturbances by the valve elements. As a result there are minimal energy losses, minimal pressure drop across the valve and prevention of trauma to the blood. Furthermore the walls of the housing 1 limit not only the pivoting of the leaflets 3 but also inhibit penetration of the connective tissue and surrounding heart structures inside the housing 1, thus preventing restriction of mobility of the leaflets 3.

When excess pressure is created at the outlet of the prosthesis the blood backflow II starts to form, which works on the conical surfaces 5b of the leaflets 3 and causes the leaflets 3 to pivot around the axis 0-0 into the closed position, because the surface generatrix 5b of the leaflets 3 is located at an angle to the axis of the blood backflow II. In this connection the convex spherical surfaces 13 in the leaflet slots 9 interact with the concave spherical surfaces 11 of the console projections 8 at the inner surface 2 of the housing 1 forming a hinge which provides a mobile connection of the leaflets 3 with the housing 1. When the side surfaces 7 contact the ledges 14 at the inner surface 2 of the housing 1 the pivoting of the leaflets 3 stops and the heart valve prosthesis closes. The leaflets 3 interact among themselves with the coaptation surfaces 6 and simultaneously with the ledges 14 at the inner surface 2 of the housing 1 by their side surfaces restricting the blood backflow II and sealing the heart valve prosthesis. The presence of small clearances between the surfaces 13 and 11 in the hinge joints of the leaflets 3 within the housing 1, as well as between the surfaces 7 and 2 in the zone of location of the projection 8, and also at portions of the surfaces 6 ensures the reduction of the mechanical trauma to the formed elements of the blood and provision of the clinically insignificant blood backflow II which washes out the surfaces 2, 6, 11, and 13 and prevents the initiation of the thrombus formation process.

Information sources:
1. Heart valve prosthesis. RF Patent No. 2113191
2. Heart valve prosthesis. Application for RF Patent No. 2006110832 A

What is claimed is:

1. A heart valve prosthesis comprising an annular housing having an inner surface defining an area of blood flow through the prosthesis, a plurality of leaflets pivotably mounted within the annular housing around a reference axis of rotation between an open position which allows the passage of direct blood flow and a closed position which restricts blood backflow, each leaflet having an upstream surface facing the direct blood flow, a downstream surface facing the blood backflow, a coaptation surface interacting with a corresponding coaptation surface of another leaflet when in a closed position, and a side surface interacting with the inner surface of the housing, at least two console projections radially oriented and directed perpendicular to the reference axis of leaflet rotation and being provided at the inner surface of the housing, and a slot embracing only one corresponding console projection of the housing and being provided at each leaflet, wherein surfaces interacting with the leaflet slots and forming a supporting part of a hinge are provided at lateral sides of the at least two console projections and counterpart surfaces forming a mobile part of the hinge and facing the side surface of the corresponding console projection are provided at inner sides of the leaflet slots of each leaflet in such a way that each console projection is located within the corresponding leaflet, wherein each console projection has two concave spherical surfaces each of which interacting with the counterpart element with convex spherical surfaces located in the slot of each leaflet, wherein the inner surface of the housing is substantially cylindrical and a part of the downstream surface of each leaflet is formed by the cylindrical surface, wherein a diameter of a cylindrical downstream surface of the leaflet corresponds to a diameter of the inner surface of the housing, and in an opened position of the leaflet a generatrix of the cylindrical part of the downstream surface is substantially parallel to a central axis of the housing.

2. A heart valve prosthesis according to claim 1, wherein the downstream surface of each leaflet is formed by the crossing cylindrical and conical surfaces.

3. A heart valve prosthesis according to claim 2, wherein the upstream surface of each leaflet is provided in a form of a cylindrical surface with a diameter equal to or larger than the diameter of the inner surface of the housing, and in the open position of the leaflet a generatrix of the cylindrical upstream surface is approximately parallel to the central axis of the housing.

4. A heart valve prosthesis according to claim 1, wherein ledges interacting with the side surfaces of the leaflets in the closed position are provided at the inner surface of the housing.

* * * * *